United States Patent [19]

Babior et al.

[11] Patent Number: 4,471,051

[45] Date of Patent: Sep. 11, 1984

[54] STABILIZATION OF NEUTROPHILS AND PLATELETS

[75] Inventors: Bernard M. Babior, Lexington, Mass.; Irena I. Aviram, Tel Aviv, Israel

[73] Assignee: New England Medical Center Hospitals, Inc., Boston, Mass.

[21] Appl. No.: 503,517

[22] Filed: Jun. 13, 1983

[51] Int. Cl.³ .................... C12N 5/00; A61K 35/14
[52] U.S. Cl. ........................................ 435/2; 424/101
[58] Field of Search ............................ 435/2; 424/101

[56] References Cited

U.S. PATENT DOCUMENTS

| 4,110,161 | 8/1978 | Sekhar | 435/2 |
| 4,344,936 | 8/1982 | Soslau | |
| 4,390,619 | 6/1983 | Pittiglio | 435/2 |
| 4,391,909 | 7/1983 | Lim | 424/94 |

OTHER PUBLICATIONS

Kotelba–Witkowska et al., Transfusion, vol. 22, 121–124 (1982).

Primary Examiner—Sam Rosen

[57] ABSTRACT

Neutrophils and platelets from human blood are stabilized for storage and subsequent reconstitution for use by reacting with a chemical cross-linking agent having functional groups reactive to form covalent linkages with the neutrophils or platelets, the functional groups being covalently bonded to a molecular backbone including a group subject to cleavage under conditions which are non-destructive of the neutrophils or platelets. After storage at reduced temperature, the composition can be reconstituted by cleavage and substantially regains its original physiological properties.

16 Claims, No Drawings

STABILIZATION OF NEUTROPHILS AND PLATELETS

This invention was made with Government support and the U.S. Government has certain rights in the invention.

This invention relates to the stabilization or preservation of human neutrophils or platelets and pertains more specifically to the treatment of such cells with a cleavable cross-linking agent for storage at reduced temperature. The cells can be reconstituted for use after storage by cleaving the cross-linking agent so that they substantially regain their original physiological properties.

Although there has been an extensive development of blood banks for collecting human blood and separating it into several different components such as red cells, white cells including neutrophils, platelets, and serum, the maximum physiological or therapeutic use of the components can be made only if they are capable of being stored until needed and/or transported to the place of need. Certain components such as red blood cells and serum can be stored for long periods after freezing under certain conditions, then reconstituted for use. Limited storage of platelets is possible, but they lose their ability to function after at most five days of storage at temperatures above freezing; and the freezing of platelets for storage, though feasible (Kotelba-Witkowska et al., Transfusion, Vol. 22, 121 ff. (1982) is an expensive and little known technique. Neutrophils, on the other hand, have been subject to agglutination or clumping after storage for as little as 48 hours at temperatures above freezing and so have had to be used within two days of preparation; storage of neutrophils by freezing has met with no success.

It has now been found that neutrophils as well as platelets can be effectively stabilized for storage over extensive periods of time provided they are first reacted with a chemical cross-linking agent having at least two functional groups reactive with protein and which includes a group subject to cleavage under conditions which are non-destructive of said neutrophils and platelets, to form covalent chemical linkages. The cross-linking agent preferably includes a molecular backbone; the backbone preferably has a length between functional groups equal to a chain of 4 to 16 carbon atoms. After storage, the neutrophils or platelets can be reconstituted for use simply by cleavage of the cross-linking agent.

A variety of cross-linking agents can be employed in the present invention; any of those which contain in addition to the cleavable group at least two functional groups which are reactive with protein and which are covalently bonded to the molecular backbone of the cross-linking agent can be used. The functional group can be any of those which form covalent linkages with protein; particularly preferred are acylating groups such as N-hydroxysuccinimide esters and imido esters. The length of the molecular backbone between the functional groups can vary over a considerable range but preferably has a length equivalent to a chain of 4 to 16 carbon atoms. The cleavable group included in the backbone between the functional groups can be any group subject to cleavage under mild conditions which are non-destructive of the cells, and include such groups as disulfides, thiosulfonates, and vicinal glycols. The disulfides and thiosulfonates can be cleaved with a reducing agent, preferably a mercaptan such as dithiothreitol; the vicinal glycols can be cleaved by reaction with an oxidizing agent such as periodic acid or periodates. In some cases, substantial cleavage occurs simply by resuspending the cross-linked cells in physiologically acceptable buffer solution and incubating at 37° C. for 20 minutes or more. Among suitable cleavable cross-linking agents which can be employed in the present invention are compounds having the following structures:

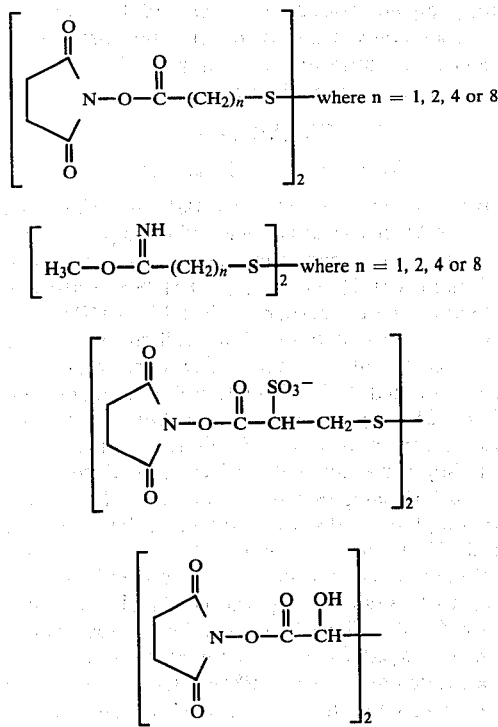

Tests have shown that neutrophils which have been reacted in accordance with the present invention, stored at low temperature, e.g. below 5° C., and then reconstituted by cleavage of the cross-linking agent, largely retain all of the desired physiological properties and are substantially free from agglutination or clumping. In particular, they are capable of ingesting and killing opsonized microorganisms. Platelets which have been reacted in accordance with the present invention and reconstituted also regain to a substantial extent their physiological and therapeutic properties, including aggregation in response to suitable reagents such as adenosine diphosphate and release of such agents as serotonin, etc.

The following specific examples are intended to illustrate more fully the nature of the present invention without acting as a limitation upon its scope.

EXAMPLES

Several different 1.0 ml quantities of Hank's balanced salt solution (hereafter HBSS), each containing $10^7$ neutrophils, were incubated at room temperature with different quantities of Lomant's reagent, the disulfide of N-hydroxysuccinimidyl 3-mercaptopropionate, after which each incubation was stopped by diluting the cell suspension with 15 ml of ice-cold HBSS. The quantities were chosen to provide concentrations of 0.1, 0.2, and 0.4 mM of cross-linker and the incubation times ranged from 1 to 12 minutes. Following these incubations, the cells were centrifuged, washed by suspending in HBSS without cross-linker, and assayed for their ability to produce superoxide ($O_2^-$) in response to phorbol myristate acetate (50 μg/ml) and for neutrophil glycolysis (measured as lactate production). The reaction with cross-linker had little effect on neutrophil glycolysis but produced powerful inhibition of superoxide production, both of which are physiological functions of neutrophils. Reaction of neutrophils with a monofunctional acylating agent, N-hydroxysuccinimidyl butyrate, at even higher concentrations for the same time periods produced very little effect on any of the neutrophil functions, even superoxide production.

EXAMPLE 2

Treatment with Cross-Linker

Neutrophils ($5 \times 10^6$ cells in HBSS) were incubated with 0.4 mM of the crosslinker of Example 1 for 3.5 minutes at room temperature. The cell suspension was then diluted with 20 ml of ice-cold HBSS, centrifuged, and the cells were resuspended in 1.25 ml HBSS.

Two-tenths ml portions of this cell suspension were then treated as follows: sample 1 was kept on ice; sample 2 was diluted with 1.8 ml HBSS, then incubated at 37° C. for 25 minutes; sample 3 was diluted with 1.6 ml HBSS, incubated at 37 for 25 minutes, then placed on ice and supplemented with 0.2 ml cold dithiothreitol (DTT), 0.1 M; samples 4 and 5 were diluted with 1.6 ml HBSS, supplemented with 0.2 ml 0.1 M DTT, and incubated at 37° C. for 25 minutes. All the samples were then chilled on ice. The cells were isolated by centrifugation, washed with 4 ml portions of Dulbecco's phosphate-buffered saline (PBS), and finally suspended in PBS and assayed for $O_2^-$ production in response to phorbol myristate acetate (PMA). Control cells were treated in exactly the same manner except that they were not incubated with the crosslinker. The results were as follows:

| $O_2^-$ production (expressed as $A_{550}$ of reduced cytochrome c) | | |
|---|---|---|
| SAMPLE | CROSSLINKER-TREATED | CONTROL |
| 1 | 0.05 | 0.74 |
| 2 | 0.37 | 0.62 |
| 3 | 0.37 | 0.53 |
| 4 | 0.48 | 0.58 |
| 5 | 0.56 | 0.59 |

These results show that the effects of the crosslinker on neutrophil $O_2^-$ production are reversed by cleavage of the crosslinker. Full reversal occurs when the crosslinker-treated cells are incubated with DTT, a powerful disulfide-cleaving reagent, but substantial (though incomplete) reversal occurs when the cells are incubated at 37° C. even in the absence of DTT.

EXAMPLE 3

Cells were treated with crosslinker as described in Example 1. The cell suspension was divided into 6 portions, and incubated at 37° C. for 30 minutes. An amount of DTT to provide a final concentration 0.01 M was added to the various portions, at intervals as indicated below. At the end of the 30 minutes incubation, the cells were chilled, centrifuged, washed, resuspended in PBS and assayed for $O_2^-$ production as described in Example 2. Control cells were treated in exactly the same way, except that they were not incubated with the crosslinker. The results were as follows:

| $O_2^-$ production (expressed as $A_{550}$ of reduced cytochrome c) | | |
|---|---|---|
| SAMPLE | DURATION OF EXPOSURE to DTT (min) | CROSSLINKER-TREATED | CONTROL |
| 1 | 0 | 0.24 | 0.49 |
| 2 | 5 | 0.25 | — |
| 3 | 10 | 0.26 | 0.36 |
| 4 | 15 | 0.25 | 0.43 |
| 5 | 20 | 0.35 | 0.49 |
| 6 | 30 | 0.40 | 0.41 |

These results confirm the results of Example 2, and show that the excess $O_2^-$-forming activity resulting when the reversing incubation is performed in the presence of DTT is only seen after several minutes of incubation with this disulfide-cleaving reagent.

EXAMPLE 4

Neutrophils were treated with crosslinker as described in Example 1, except that the resuspension in HBSS was at a concentration of $2 \times 10^7$ cells/ml. Three 0.7 ml portions of the cell suspension were each mixed with 1.1 ml of HBSS, then treated as follows: Sample 1 was kept on ice, and after 25 minutes received 0.2 ml 0.1 M DTT; sample 2 was incubated at 37° C. for 25 minutes, then received 0.2 ml 0.1 M DTT; sample 3 received 0.2 ml 0.1 M DTT, then was incubated at 37° C. for 25 minutes. The cells were then chilled, centrifuged, washed and resuspended in PBS for functional studies. $O_2^-$ production in response to phorbol myristate acetate was assayed as described previously; the secretion of specific granule contents in response to the same stimulus was determined by measuring the release of cobalamin-binding protein into the supernatant according to a well-established technique. Control cells were treated exactly the same way except that they were not incubated with the crosslinker. The results were as follows:

| | Function (as % of control sample 1) | | | |
|---|---|---|---|---|
| | $O_2^-$ Production | | Degranulation | |
| Sample | X-linker | Control | X-linker | Control |
| 1 | 7 | (100) | 2 | (100) |
| 2 | 29 | 92 | 12 | 67 |
| 3 | 83 | 87 | 14 | 35 |

$O_2^-$ production was blocked reversibly by crosslinker as previously described. Degranulation was also blocked by crosslinker, but cleavage of the crosslinker resulted in a modest recovery of this process. To a large extent, the impairment in degranulation even after cleavage of the crosslinker seemed to reflect a loss in degranulating power during the course of the incubation at 37° C., since degranulation by control cells also fell substantially during this incubation.

EXAMPLE 5

It was observed that crosslinker-treated cells which had been stored overnight in the refrigerator were as easy to suspend in buffer as freshly prepared cells. Untreated neutrophils, however, agglutinated into a single gelatinous mass after overnight storage. Because $O_2^-$ production is a primary function of neutrophils, this function was examined in crosslinker-treated neutrophils which had been stored for several days at 4° C. Cells were treated with crosslinker as described in Example 1, then stored for the times indicated, and finally reactivated by incubation for 25 minutes at 37° C. with DTT. $O_2^-$ production in response to PMA was assayed as described. The results were as follows:

| Duration of Storage (Days) | $O_2^-$ Production (% of unstored control) Crosslinked | Control |
|---|---|---|
| 0 | 14* | (100) |
| 1 | 50 | — |
| 6 | 40 | 0 |

*Not reactivated

The cells which had been reacted went freely into suspension upon agitation even after 6 days of storage; the control cells had completely agglutinated by this time. $O_2^-$ production was well preserved during the 6 day storage period.

EXAMPLE 6

Phagocytosis

Neutrophils were treated with crosslinker as described in Example 1 except that they were resuspended in HBSS at a concentration of $9.6 \times 10^7$ cells/ml. Cells were then treated as follows: Sample 1 was incubated with 0.01 M DTT for 25 minutes at 37°; sample 2 was kept on ice. The cells were then centrifuged, washed and resuspended in HBSS at a concentration of $9.6 \times 10^7$ cells/ml. Control cells obtained and assayed on a different day were also suspended in HBSS at $9.6 \times 10^7$ cells/ml. Phagocytosis was then assayed by measuring the uptake of emulsified mineral oil droplets tinted with Oil Red O according to a well-established method. The results of this experiment were as follows:

| Sample | Phagocytosis (Oil Red Absorbance/8'/1.5 × 10⁸ cells) |
|---|---|
| X-linked | 0.04 |
| X-linked and Cleaved | 0.15 |
| Control | 0.13 |

These results indicate that, like $O_2^-$ production, phagocytosis is reversibly inhibited by treating neutrophils with a cleavable crosslinker.

What is claimed is:

1. The method of stabilizing for storage neutrophils or platelets obtained from blood which comprises reacting them with a chemical cross-linking agent having at least two functional groups reactive with protein and which includes a group subject to cleavage under conditions which are non-destructive of said neutrophils and platelets, to form covalent chemical linkages.

2. The method as claimed in claim 1 in which said functional groups are covalently bonded to a molecular backbone which has a length between said functional groups equal to a chain of 4 to 16 carbon atoms.

3. The method as claimed in claim 2 in which said functional groups are acylating groups.

4. The method of stabilizing neutrophils as claimed in claim 1.

5. The method as claimed in claim 1 including the additional step of cooling said neutrophils or platelets to a temperature below 5° C.

6. The method as claimed in claim 1 in which neutrophils or platelets are reacted with a cross-linking agent in which said cleavable group is a disulfide linkage.

7. The method as claimed in claim 2 in which neutrophils or platelets are reacted with a cross-linking agent in which said cleavable group is a disulfide linkage.

8. The method as claimed in claim 7 comprising the additional step of reconstituting said neutrophils or platelets by cleaving said cleavable group.

9. The method as claimed in claim 8 in which said neutrophils or platelets are cleaved by reacting with a reducing agent.

10. The method as claimed in claim 9 in which said reducing agent is a mercaptan.

11. The method as claimed in claim 10 in which said cross-linking agent is the disulfide of N-hydroxysuccinimidyl 3-mercaptopropionate.

12. The method as claimed in claim 10 in which said mercaptan is dithiothreitol.

13. Neutrophils or platelets from blood stabilized for storage and reconstitutable for subsequent use, said neutrophils or platelets being covalently bonded by a chemical cross-linkage which includes a group subject to cleavage under conditions which are non-destructive of said neutrophils and platelets.

14. Neutrophils as claimed in claim 13 in which said cleavable group is a disulfide linkage.

15. A kit for stabilizing neutrophils and platelets for storage at low temperature comprising
    a supply of chemical cross-linking agent having at least two functional groups reactive with protein and which includes a group subject to cleavage under conditions which are non-destructive of said neutrophils and platelets, and
    a supply of cleaving agent for cleaving said cleavable group.

16. A kit as claimed in claim 15 in which said functional groups are acylating groups, said agent includes a molecular backbone having a length between said functional groups equivalent to a chain of 4 to 16 carbon atoms, said cleavable group is a disulfide group, and
    said cleaving agent comprises a reducing agent capable of breaking said disulfide group.

* * * * *